United States Patent [19]
Chapman

[11] 4,192,825
[45] Mar. 11, 1980

[54] ENERGY EFFICIENT ALKYLATION PROCESS

[75] Inventor: Charles C. Chapman, Bartlesville, Okla.

[73] Assignee: Phillips Petroleum Company, Bartlesville, Okla.

[21] Appl. No.: 922,478

[22] Filed: Jul. 7, 1978

[51] Int. Cl.² .............................................. C07C 3/54
[52] U.S. Cl. .................................... 585/719; 585/910
[58] Field of Search .................... 260/683.48, 683.49, 260/683.62, 683.42

[56] References Cited

U.S. PATENT DOCUMENTS

| | | | |
|---|---|---|---|
| 2,542,927 | 2/1951 | Kelley | 260/683.48 |
| 2,910,521 | 10/1959 | Cobb, Jr. | 260/683.48 |
| 3,073,878 | 1/1963 | Johnson | 260/683.48 |
| 3,204,010 | 8/1965 | Van Pool | 260/683.42 |
| 3,763,022 | 10/1973 | Chapman | 260/683.48 |
| 3,855,344 | 12/1974 | Jones | 260/683.49 |
| 3,857,904 | 12/1974 | Chapman | 260/683.48 |
| 3,925,501 | 12/1975 | Putney et al. | 260/683.48 |
| 4,059,649 | 11/1977 | Chapman et al. | 260/683.48 |

Primary Examiner—George Crasanakis

[57] ABSTRACT

In an acid catalyzed alkylation system, a prefractionated reactor hydrocarbon effluent bottoms stream, substantially free of HF, is passed to a propane concentrator in order to provide for a more concentrated and desirable feed for the depropanizer. Due to the highly concentrated propane stream fed to the depropanizer, the size of the depropanizer can be much smaller thereby saving in energy. Hot overhead vapor from the isostripper is also passed in an indirect heat exchange relationship with various feed streams and fractionators in order to supply heat for the preheating of the feed streams and the reboiling of the fractionators. The bottoms fraction of the isostripper can also be passed in an indirect heat exchange relationship with various feed streams and fractionators. The alkylation process, therefore, maximizes the use of available waste heat and reduces the pressure and utilities on the depropanizer thereby saving greatly on energy costs.

12 Claims, 4 Drawing Figures

ENERGY EFFICIENT ALKYLATION PROCESS

BACKGROUND OF THE INVENTION

This invention relates to a process for alkylating an alkylatable isoparaffinic hydrocarbon with olefinic hydrocarbons. In another aspect, this invention relates to a process for the alkylation of isoparaffins which employs various energy conservation techniques. In yet another aspect, this invention relates to an alkylation process wherein a prefractionator is used to separate out substantially all of the acid catalyst prior to passing the alkylation zone hydrocarbon to a depropanizer and isostripper. In still another aspect, this invention relates to an alkylation process wherein a propane concentration zone is utilized to increase the concentration of propane in the feed stream to the depropanizer. Still another aspect of this invention relates to the isostripper overhead and bottoms being passed in an indirect heat exchange relationship with feed streams and fractionators in order to supply heat necessary for the preheating or reboiling of said feed streams and fractionators. In still another aspect, this invention relates to an alkylation process which utilizes a fractionation column for raising the propane concentration in the feed stream fed to the depropanizer. In still another aspect, this invention relates to an alkylation process which uses at least one flashing zone to increase the propane concentration in the feed stream to the depropanizer. Still another aspect of this invention relates to the use of the overhead vapor stream from the isostripper as the heat exchange medium for the heating or reboiling of the prefractionation zone in the alkylation process in the use of the bottoms stream of the isostripper as a heat exchange medium to preheat feed stream to the isostripper. Since there is substantially no HF in the feed to the isostripper, this column can then be operated without corrosion problems at relative high pressure and high temperature.

Alkylation of isoparaffinic hydrocarbons with olefinic hydrocarbons is well known as a commerically important method for producing gasoline boiling range hydrocarbons. Generally, the alkylation of isoparaffins with olefins is accomplished by contacting the reactants with an acid-acting catalyst, settling the mixtures to separate the catalyst from hydrocarbons, and further separating the hydrocarbon stream into its various components, i.e., alkylate product. The alkylate is typically a mixture of isomers of heptane, octane, etc., with the exact composition depending upon the isoparaffin and olefin reactants used. Various types of catalysts have been utilized in this reaction, including sulfuric acid, hydrofluoric acid, phosphoric acid, certain halosulfonic acids, and aluminum chloride. The preferred acid catalyst, however, is hydrofluoric acid because of the relative ease with which it can be regenerated and reused and because of the superior quality of the alkylate that is produced.

The energy requirements and costs of an alkylation process can be great and it is therefore desirable to maintain the energy requirements for an alkylation process at a low level. This is particularly important where energy is valuable and the products for generating energy are in relatively short supply and expensive. It has been discovered that by maximizing the use of available waste heat in the system and decreasing the pressure and use of utilities on the depropanizer, that the energy requirements of an alkylation process can be reduced thereby resulting in great energy savings.

Accordingly, it is an object of this invention to provide an improved alkylation process wherein the energy requirements are reduced.

Another object of this invention is to reduce the pressure and utilities on the depropanizer thereby resulting in the energy savings.

Still another object of this invention is to provide an efficient alkylation process which maximizes the possible use of available waste heat in the system.

Other aspects, objects, and advantages of the present invention will become apparent from a study of the disclosure, the appended claims, and the drawings.

SUMMARY OF THE INVENTION

This invention relates to an acid catalyst alkylation system wherein an olefin and isoparaffin is contacted in the presence of an acid alkylation catalyst under alkylation conditions to form an alkylation effluent comprising alkylate, isoparaffin, acid catalyst, and nonreacted olefins. The alkylation effluent is then separated into an acid catalyst phase and the hydrocarbon phase with the hydrocarbon phase being passed to a prefractionation zone. The hydrocarbon phase is separated into at least two fractions with a substantially HF free fraction being passed to a propane concentration zone in order to increase the concentration of propane in the feed stream to be sent to the depropanizer. Utilizing the propane concentration zone allows the use of a smaller depropanizer unit with a reduction in pressure and utilities.

In one embodiment of the invention, the propane concentration zone is a fractionation column with the propane-rich overhead being passed on to the depropanizer in order to remove propane from the system. In another embodiment, the propane concentration zone is a flashing zone yielding propane-rich flashed vapor which is fed to the depropanizer.

The alkylation process also embodies feeding an isoparaffin and alkylate-rich stream, substantially free of HF, to an isostripper to yield an overhead vapor stream and a bottoms stream. The isoparaffin and alkylate-rich stream can be obtained from, for example, the prefractionator or the propane concentrator.

The hot overhead vapor from the high pressure, high temperature isostripper is used as a heat exchange medium and passed in indirect heat exchange relationship with at least one of the various feed streams or fractionation zones of this system. The isostripper bottoms can also be used in the role of a heat exchange medium. The use of the isostripper vapor overhead and bottoms in this manner allows for substantial energy savings in that it maximizes the use of available waste heat energy.

DETAILED DESCRIPTION OF THE INVENTION

Figure 1:
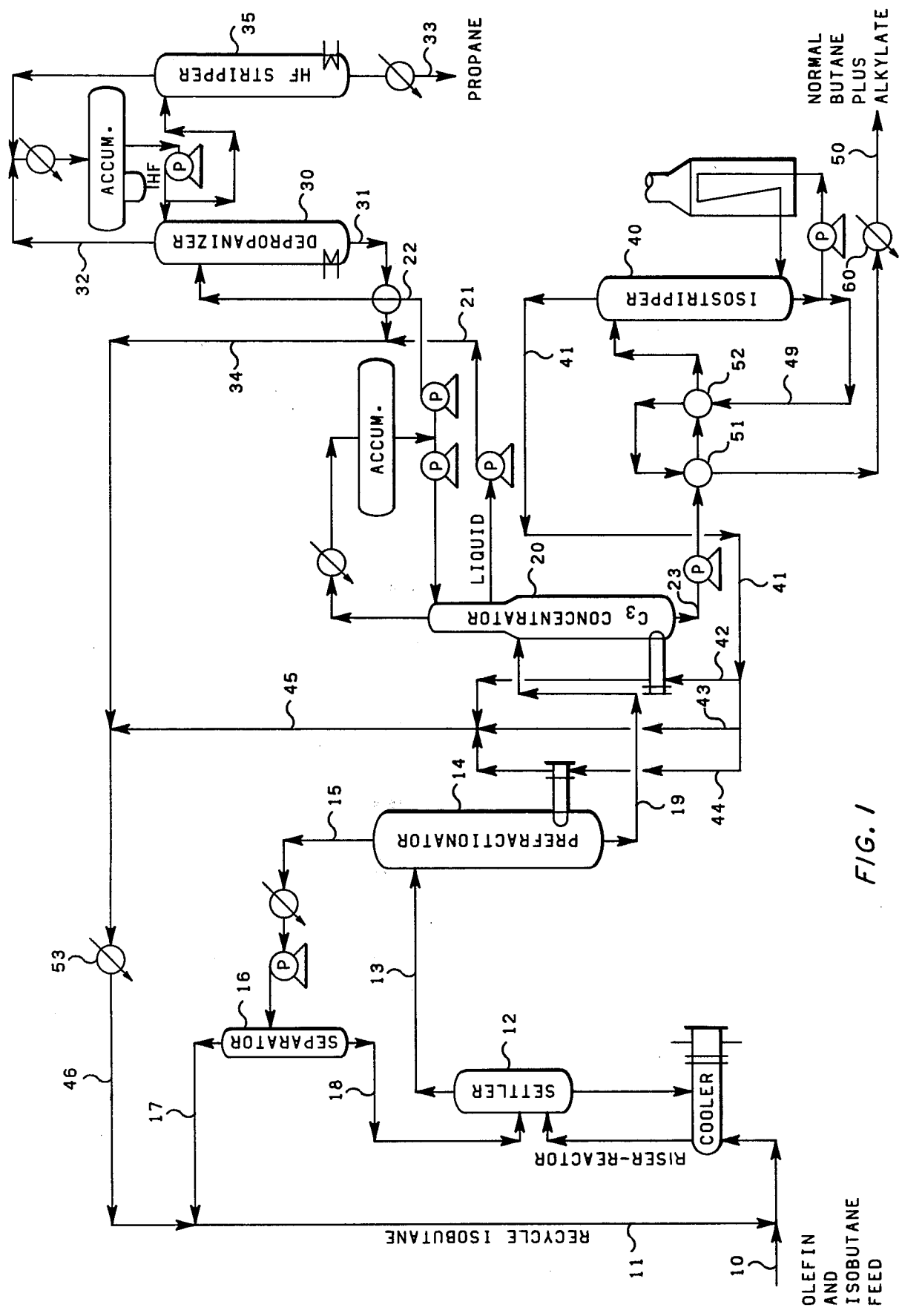
FIG. 1 is a schematic of an embodiment of the present invention in which the propane concentration zone is a fractionation column and the isostripper vapor is used to reboil the propane concentrator and the prefractionator.

This invention relates to an alkylation process wherein energy requirements are reduced by maximizing the use of available waste heat from the system and reducing the pressure and utilities used in the depropanizer. Upon contacting an olefin and isoparaffin in the presence of an acid alkylation catalyst to yield an alkylation reactor effluent, the effluent is passed into a settler in order to separate the effluent into an acid catalyst phase and a hydrocarbon phase. The liquid hydrocarbon phase is then passed to a prefractionation zone which separates the hydrocarbon phase into at least two fractions. The type of column used for the prefractionation zone is well known in the art and the function of the prefractionation zone is to separate substantially all of the remaining acid catalyst in the hydrocarbon phase so that a substantially acid catalyst-free hydrocarbon stream can be recovered and passed to further separation, i.e., the depropanizer and isostripper.

The acid-catalyst-free stream is passed from the prefractionation zone to a propane concentration zone to thereby increase the concentration of propane in the feed stream to be sent to a depropanizer. The propane-rich fraction recovered from the propane concentration zone is sent to a depropanizer from which purified propane is recovered. The propane concentration zone can be any suitable device for separating and concentrating propane in a particular stream, but the preferred propane concentration zones are that of a flashing zone and a fractionation column. The propane concentration zone increases the propane content in this propane-rich stream about five to about forty times the propane content in the feed to the propane concentration zone.

An isoparaffin and alkylate-rich stream is passed through an isostripper yielding a hot overhead vapor isoparaffin stream and a bottoms stream containing alkylate. The feed stream to the isostripper can be obtained from either the bottoms fraction of the prefractionator or the propane concentration zone. The isoparaffin and alkylate-rich stream is that stream which is rich in isoparaffin and alkylate product and from which alkylate production is ultimately to be recovered. The propane concentration zone increases the isobutane and alkylate concentration in this isobutane and alkylate-rich stream in that amount of material removed in the propane-rich stream.

The hot overhead vapor from the high pressure, high temperature isostripper, as well as the bottoms stream of the isostripper, can be used as a heat exchange medium in order to preheat a feed stream or reboil fractionation columns. The heat in the overhead and bottoms streams is usually wasted as the streams are cooled by independent heat exchange mediums before being passed to storage or recycled to the alkylation medium. By passing the streams in indirect heat exchange relationship with at least one feed stream or fractionation zone, the waste heat is used effectively to reduce the energy requirements of the alkylation system. Substantial energy savings can be realized by maximizing the use of this available waste heat energy.

Any appropriate olefin and isoparaffin can be used in conjunction with the process of this invention as long as the olefin and isoparaffin are amenable to alkylation. The particular olefin and isoparaffin used will depend on the type of alkylate product desired. Examples of appropriate olefins are the $C_3$–$C_7$ olefins wherein the preferred olefins are propylene and the butylenes. Examples of appropriate isoparaffins are the $C_4$–$C_8$ isoparaffins with the preferred isoparaffin being isobutane.

Various types of catalysts can be utilized in the process, including sulfuric acid, hydrofluoric acid, phosphoric acid, certain halosulfonic acids, and aluminum chloride. The preferred catalyst, however, is hydrofluoric acid because of the relative ease with which it can be regenerated and reused and because of the superior quality of the alkylate that is produced.

The particular type of reactor to be used in the process is not important and many appropriate reactors are well known in the art. The preferred type of reactor, however, is that of the riser reactor, e.g., as in U.S. Pat. No. 3,213,157.

As for reaction conditions, the invention is not dependent upon specific reaction conditions as appropriate reaction conditions are conventional and well known in the art. However, the mole ratio of isoparaffin to olefin is usually maintained somewhere in the range of 4:1 to 20:1. The volume ratio of acid catalyst to hydrocarbon feed can be maintained at about 4:1 but can be varied in the range of about 0.5:1 to about 6:1. The particular temperature at which the reaction is run will depend upon the particular olefin used in the alkylation. Sufficient pressure is used to maintain liquid phases.

High pressure and high temperature can be used in the isostripper (no corrosion) due to the separation of substantially all the acid catalyst from the hydrocarbon phase in the prefractionation zone thereby allowing a substantially acid catalyst-free isoparaffin and alkylate stream to be fed to the isostripper. It is desirable to run the isostripper at a high pressure because the overhead vapor stream is then at a high temperature and is that much more effective as a heat exchange medium in preheating feed streams and reboiling fractionation zones.

In one specific embodiment of the invention, the hydrocarbon phase from the acid catalyst alkylation settler, the preferred acid catalyst being hydrofluoric acid, is charged to a prefractionator, preferably a low pressure prefractionator, requiring no pumping from the reactor settler. The overhead vapor from the prefractionator is condensed and pumped to a phase separator to separate the HF catalyst from the hydrocarbon. The HF catalyst and the hydrocarbon phase are then separately recycled to alkylation. The bottoms liquid from the prefractionator is charged to a propane concentration column. Overhead vapor from the propane concentration column, which is a fractionation column, is charged to a depropanizer-HF stripper operation to prodcue yield propane. Bottoms liquid from the depropanizer is returned to alkylation. Optionally, a side draw from the propane concentration column, which is rich in isobutane, can be removed therefrom and recycled to alkylation.

Bottoms liquid from the propane concentration column is then pumped as feed to a high pressure, high temperature isostripper. The hot isoparaffin overhead vapor from the isostripper is then used to indirectly reboil both the prefractionator and the propane concentration column. The isoparaffin vapor is then recycled, after further cooling and condensing, to alkylation.

Bottoms liquid from the isostripper can be passed in indirect heat exchange relationship with the feed stream to the isostripper in order to preheat said feed stream. The bottoms liquid from the isostripper is then passed to storage as alkylate product.

Another specific embodiment of the invention involves the use of a flashing zone as the propane concentration zone. Hydrocarbon phase from the alkylation settler is passed to a prefractionation zone, preferably a low pressure prefractionator so no pumping of reactor hydrocarbon is required. Bottoms liquid from the prefractionator is flashed at a relatively low pressure after having been indirectly preheated with hot isoparaffin vapor from the high pressure, high temperature isostripper. Liquid from the low pressure flash is then pumped to the isostripper. Vapor from the flash is condensed and the liquid is pumped to high pressure, indirectly heated with hot alkylate product from the isostripper, and charged to a second relatively high pressure flash. Liquid from the second flash is cooled and recycled to alkylation along with the cooled, condensed isobutane stripper overhead and the cooled bottoms from the subsequently described depropanizer. Vapor from the second flash, substantially HF-free and containing propane concentrate is charged to the depropanizer. Overhead from prefractionation is condensed and sent to a phase settler from which HF is recovered and recycled to alkylation. A hydrocarbon phase is also recycled to alkylation. When ethylene is present as an olefin, however, at least a portion is preheated and also charged to the depropanizer.

The depropanizer and HF stripper of this can utilize separate condenser-accumulator systems. The depropanizer can be operated at relatively high temperature since substantially no acid catalyst, hydrofluoric acid, is charged thereto. The HF stripper produces its own reflux (hydrocarbon) and can return acid catalyst (if any) to HF alkylation.

In another specific embodiment of the invention, hydrocarbon phase from the alkylation settler is charged to a low pressure prefractionation zone with the bottoms from the prefractionator indirectly preheating the prefractionator feed. Bottoms from the HF stripper is then blended with the prefractionator bottoms and this blend indirectly preheats the isostripper feed. The blend is then indirectly cooled and flashed to indirectly cool the recycle alkylation catalyst from the settler. The flashed mass can then be charged to a first liquid-vapor separator with the bottoms liquid from the separator, in part, returned to the prefractionator bottoms upstream of the flashing thereof. The other part of the bottoms liquid is used as a feed stream to the isostripper.

Vapor from the liquid-vapor separator is compressed and condensed and is pumped as feed to the depropanizer. A portion of the HF stripper bottoms can be combined with the vapor as feed to the depropanizer. The depropanizer bottoms is used to indirectly preheat the feed to the depropanizer. Overhead from the depropanizer is recovered as propane yield.

The prefractionator overhead is condensed and contacted with HF-rich overhead from the HF stripper for removal of organic fluorides from the hydrocarbon into the HF liquid which is recycled to alkylation. The separated, treated hydrocarbon is indirectly preheated with HF stripper bottoms and is charged to the HF stripper as feed therefor.

High pressure, high temperature isobutane vapor overhead from the isostripper indirectly reboils the prefractionator, indirectly preheats the isostripper feed, is indirectly cooled and condensed, and is then recycled to alkylation.

In another specific embodiment of the invention, the hydrocarbon liquid phase from an HF alkylation phase separator is charged to a preferably low pressure prefractionator. The prefractionator overhead vapor is condensed and pumped to phase separation. The separated liquid HF and liquid hydrocarbon phases are each separately returned to alkylation. The prefractionator bottoms liquid is pumped as feed to a preferably high pressure, high temperature isostripper.

A vapor side draw, withdrawn from just below the feed locus on the prefractionator, is removed from the prefractionator. The side draw stream is expanded and fed to a refluxed separation column which is a propane concentration zone. Bottoms liquid from the separation column is recycled to alkylation with the overhead vapor from the separation column being condensed (to produce reflux for the separation column) and the yield portion is charged to the depropanizer to yield propane. The depropanizer bottoms liquid is returned to alkylation.

The high temperature isoparaffin vapor overhead from the isostripper is then used to indirectly heat a lower liquid side draw (inner heating) of the prefractionator. The heated vapors produced in the side draw are returned to the prefractionator tower below the liquid withdrawal locus. Alkylate bottoms liquid from the isostripper can be used to indirectly reboil the prefractionator as well.

Further details of this invention will become apparent from the following detailed description of the drawings and the calculated examples. The following embodiments are not intended to limit the invention in any way and are given only for illustration of the invention.

FIG. 1 shows an HF alkylation of feed isobutane with olefin 10, e.g., propylene and/or butylenes, wherein the hydrocarbon phase 13 from the alkylation separator 12 is charged to a relatively low pressure prefractionation zone 14, wherein substantially all of the HF in the separation hydrocarbon phase is present in the overhead 15 from the prefractionator. This overhead is condensed and liquid phase separated 16, the liquid HF lower phase 18 being returned to the settler 12, and the overhead liquid from 16 is returned via 17 to HF alkylation as a portion of the recycled isobutane 11.

The prefractionator bottoms 19 is fed to propane concentration zone 20, which, in this example, is a fractionation column. Bottoms 23 from 20 is indirectly heated at 51 and 52 by isostripper yield bottoms 49 of high pressure isostripper 40, and then charged to isostripper 40. Overhead vapors 41 from the isostripper indirectly reboil the bottoms of propane concentrator 20 and prefractionator 14 via streams 42 and 44, respectively, the thusly condensed and cooled stream being returned via 45 and 46, after cooling at 53, as a portion of recycle isobutane 11. A portion of stream 41 can by-pass heating of the prefractionator 14 and propane concentrator 20 via conduit 43. Bottoms 49, cooled in exchanges 52 and 51 are removed as product, after further indirect cooling at 60 via conduit 50.

Overhead yield 22 from propane concentrator 20 is fed to depropanizer 30, after indirect heat from bottoms 31 of depropanizer 30. A liquid side cut 21, rich in isobutane, can be removed from propane concentrator 20, thereby by-passing depropanizer 30, and become a portion of the recycle isobutane 11 via 34.

Depropanizer overhead 32 is condensed and passed to an accumulator wherefrom any HF is recovered and recycled to alkylation (not shown). Liquid hydrocarbon from the accumulator is charged to HF stripper 35. Propane liquid is recovered at 33.

The operation of the invention saves about 1,600,000,000 Btu/day heat, by utilizing waste heat, as disclosed, compared to not using waste heat. The heat savings is estimated as about $4,000/day equivalent value on natural gas at $2.50/1000 SCF or $2.50/1,000,000 Btu.

No pumping is effected on the reactor effluent charged to the lower pressure prefractionation, and no pumping is effected on charging bottoms from prefractionation to the still lower pressure propane concentrator. The bottoms from the propane concentrator are pumped to the high pressure, high temperature isostripper wherefrom hot overhead vapor is recovered and used as heating source for the prefractionator and propane concentrator, the latter two units operated at relatively low pressure. The system all saves in the reduction of pressure and utilities for the depropanizer 30 due to the smaller and more concentrated feed stream 22 charged thereto.

An example operation of the system is as follows:

| Compound Stream | HF | $C_3$ | $iC_4$ | $nC_4$ | $iC_5$ plus | Total |
|---|---|---|---|---|---|---|
| (13) | 518 | 249 | 15,035 | 581 | 1,134 | 17,517 |
| (15) | 517.7 | 40 | 955 | 28 | 5 | 1,545.7 |
| (17) | 30 | 35 | 935 | 28 | 5 | 1,033 |
| (18) | 487.7 | 5 | 20 | 0 | 0 | 512.7 |
| (19) | 0.3 | 209 | 14,080 | 553 | 1,129 | 15,971.3 |
| (22) | 0.3 | 93 | 255 | 1 | 0 | 349.3 |
| (31) | 0 | 34 | 254.9 | 1 | 0 | 289.9 |
| (21) | 0 | 66 | 4,992 | 161 | 14 | 5,233 |
| (23) | 0 | 50 | 8,833 | 391 | 1,115 | 10,389 |
| (41) | 0 | 50 | 8,829 | 320 | 120 | 9,319 |
| (11) | 30 | 185 | 15,010.9 | 510 | 139 | 15,874.9 |
| (33) | 0 | 57 | 0.1 | 0 | 0 | 57.1 |
| (50) | 0 | 0 | 4 | 71 | 995 | 1,070 |

CALCULATED RUN mols/hour[a]

[a] Pound mols/hour.

OPERATING CONDITIONS

| HF Alkylation: | |
|---|---|
| Pressure, psig. | 150 |
| Temperature, °F. | 90 |
| $IC_4$/Olefin mol ratio | 20:1 |
| HF/Total Hydrocarbon, vol ratio | 4:1 |
| Prefractionator (14): | |
| Pressure, psig. | 115 |
| Top Temperature, °F. | 113 |
| Bottom Temperature, °F. | 150 |
| Propane Concentrator (20): | |
| Pressure, psig. | 95 |
| Top Temperature, °F. | 115 |
| Side Draw Temperature, °F. | 131 |
| Bottom Temperature, °F. | 141 |
| Isostripper (40): | |
| Pressure, psig | 230 |
| Top Temperature, °F. | 207 |
| Bottom Temperature, °F. | 416 |
| Depropanizer (30): | |
| Pressure, psig. | 245 |
| Top Temperature, °F. | 119 |
| Bottom Temperature, °F. | 190 |
| HF Stripper (35): | |
| Pressure, psig. | 285 |
| Top Temperature, °F. | 132 |
| Bottom Temperature, °F. | 139 |

This system has to yield, in this operation illustrated for FIG. 1, 57 pound mols of propane per hour via 33 in order to rid the system of propane charged to and produced in the alkylation operation. Without the propane concentrator 20 of my invention, it is calculated that the charge to the depropanizer 30 would have to be about 7,100 pound mols per hour from stream 19, the remainder of stream 19 being charged to the isostripper 40. This 7,100 pound mols per hour of stream 19 would contain about 93 pound mols per hour of propane in the feed to depropanizer 30. By using my propane concentrator 20, I can charge 93 pound mols per hour of propane in about 350 pound mols of feed 22 to the depropanizer 30, and thusly yield the necessary 57 pound mols of propane through conduit 33. My propane concentrator can produce a feed to the depropanizer 30 having about five to about forty times that mol percent propane concentration in the prefractionator bottoms 19.

Figure 2:
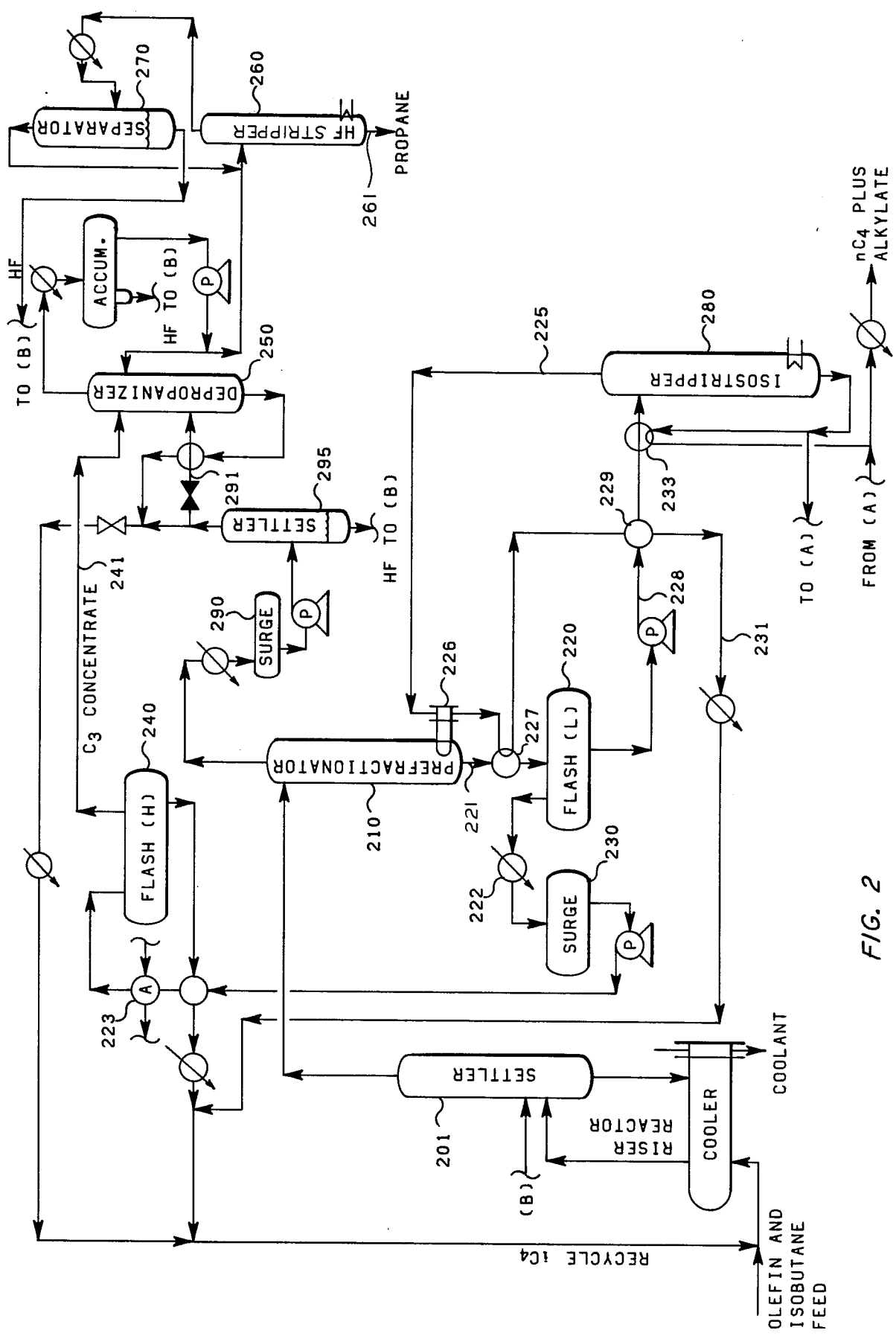
FIG. 2 is a schematic showing two flash zones functioning as the propane concentration zone.

Referring now to FIG. 2, the disclosed alkylation system of this embodiment uses low pressure flash 220 and then a high pressure flash 240 on the HF-free prefractionator bottoms 221 to concentrate the propane in the feed thereto via 241. Only that amount of propane charged in fresh feed to alkylation and that made in the alkylation has to be yielded out the HF stripper 260 via 261.

The vapor 222 from low pressure flash 220 is condensed and pumped from liquid surge tank 230 to high pressure (liquid pressure is inexpensive) and this high pressure liquid is indirectly heated with "waste heat" at 223 and subjected to high pressure flash 240, to concentrate the propane in the vapor feed to the depropanizer. There is only a trace of HF in this feed, allowing relatively low pressure operation of the depropanizer.

Hot overhead vapor 225 from isostripper 280 is passed in indirect heat exchange relationship with prefractionator 210 at 226 in order to reboil said prefractionator. The vapor is then passed in indirect heat exchange relationship with the bottoms 221 from prefractionator 210 at 227 and the feed 228 to the isostripper at 229 before being recycled to alkylation via 231.

The "waste heat" of the isostripper bottoms 232 is utilized for preheating the isostripper feed 228 at 233 and the liquid feed to the high pressure flash tank at 223.

When ethane is present in the prefractionator 210 overhead, at least a portion of the hydrocarbon from settler 295 is passed via 291 to depropanizer 250 after being indirectly heated with the bottoms from depropanizer 250.

The invention utilizes maximum waste heat and reduces the pressure and utilities on the depropanizer when butylenes are used to HF alkylate isobutane.

A calculated example of possible operating conditions is as follows:

| CALCULATED OPERATING CONDITIONS | |
|---|---|
| HF Alkylation (201): | |
| Pressure, psig. | 150 |
| Temperature, °F. | 90 |
| IC$_4$/Olefin mol ratio | 20:1 |
| HF/HC vol. ratio | 4:1 |
| Prefractionator (210): | |
| Pressure, psig. | 115 |
| Top Temperature, °F. | 115 |
| Bottom Temperature, °F. | 150 |
| Low Pressure Flash (220): | |
| Pressure, psig. | 65 |
| Temperature, °F. | 113 |
| Surge Tank (230): | |
| Pressure, psig. | 60 |
| Temperature, °F. | 100 |
| High Pressure Flash (240): | |
| Pressure, psig. | 265 |
| Temperature, °F. | 206 |
| Depropanizer (250): | |
| Pressure, psig. | 240 |
| Top Temperature, °F. | 117 |
| Bottom Temperature, °F. | 200 |
| HF Stripper (260): | |
| Pressure, psig. | 285 |
| Top Temperature, °F. | 132 |
| Bottom Temperature, °F. | 139 |
| Separator (270): | |
| Pressure, psig. | 265 |
| Bottom Temperature, °F. | 100 |
| Isostripper (280): | |
| Pressure, psig. | 230 |
| Top Temperature, °F. | 207 |
| Bottom Temperature, °F. | 416 |
| Surge (290): | |
| Pressure, psig. | 95 |
| Temperature, °F. | 100 |
| Settler (295): | |
| Pressure, psig. | 265 |
| Temperature, °F. | 100 |

Figure 3:
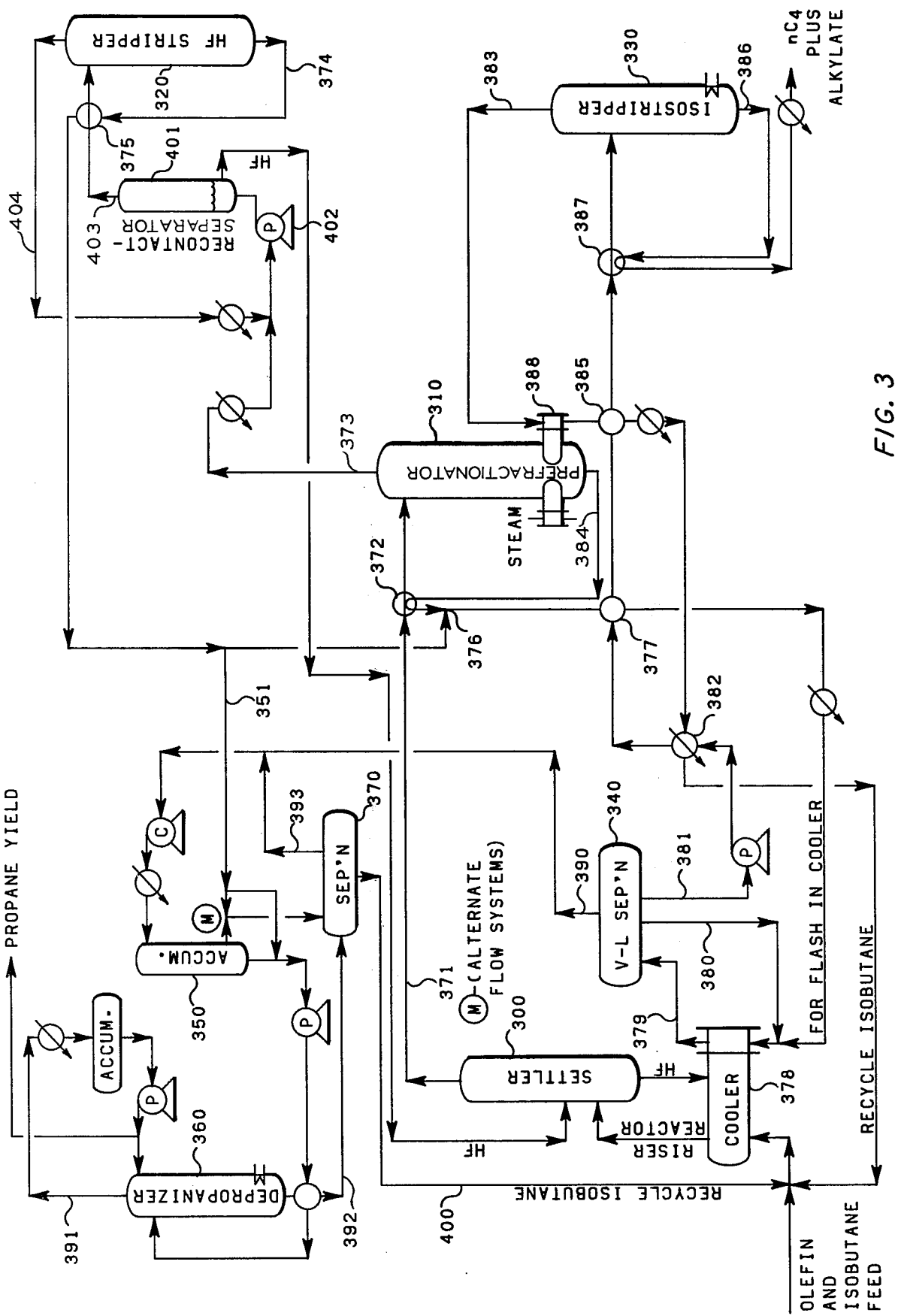
FIG. 3 is a schematic showing an embodiment of the present invention wherein prefractionator bottoms is flashed and used to cool acid catalyst cooler and also yielding a concentrated propane stream which is fed to the depropanizer. Isostripper overhead is used to reboil the prefractionator and isostripper bottoms are used to preheat the feed stream to the isostripper.

The embodiment shown in FIG. 3 discloses an alkylation system wherein the hydrocarbon phase 371 from the HF alkylation zone 300 is heated 372 and charged to prefractionator 310. Overhead 373 from 310 is charged to HF stripper 320. Bottoms 374 from 320 is recovered, heat exchanged 375 and added to the bottoms of prefractionator 310 at 376. This admixture after heat exchange 377 to further cool same, is flashed in the indirect heat exchange HF acid cooler 378, the mass flowing via 379 to liquid-vapor separator 340. Some liquid from 340 is returned to flash via 380. The "yield" portion 381 is heat exchanged at 382 with isostripper overhead 383, with prefractionator bottoms 384 at 377, again with isostripper overhead at 385 and with isostripper bottoms 386 at 387. The "yield" portion is then charged to isostripper 330. Overhead vapors 383 from 330 reboil the prefractionator 310 at 388, and after heat exchange to further cool same, i.e., 385 and 382, are returned as part of the recycled isobutane to alkylation.

Vapors 390 from separator 340 are compressed C and condensed and passed to accumulator 350, to which also some bottoms via 351 of HF stripper 320 can be added to the effluent from 350, at M.

The accumulated liquid in 350 is, in the yielded quantity, charged to the depropanizer, yielding propane overhead 391. The bottoms 392, rich in isobutane, is charged to separator 370 for recovery of recycle isobutane 400. Any vapors in 370 are returned to compressor C via 393.

HF-propane overhead vapors 404 from HF stripper 320 are condensed and added to prefractionator overhead 373 upstream of mixing pump 402 and charged to separator 401. Overhead liquid hydrocarbon 403, lean in organic fluorides, is charged to HF stripper 320.

Stream 351 from HF stripper 320 at M can be added to the effluent from accumulator 350 which flows to separator 370 and/or can be added directly to the yield from accumulator 350, depending upon composition of stream 351.

Stream 386 after exchanger 387 can be further used for heating since this stream must be further cooled prior to yielding it to storage or blending.

The invention uses waste heat and uses flash-cooling of the systems HF alkylation catalyst. The flash-cooling of the catalyst also serves the purpose of flashing the prefractionator bottoms to concentrate the propane in the feed stream charged to the depropanizer.

Exemplary operating conditions are given in the following calculated example:

| CALCULATED OPERATING CONDITIONS | |
|---|---|
| HF Alkylation (300): | |
| Pressure, psig. | 150 |
| Temperature, °F. | 90 |
| IC$_4$/Olefin mol ratio | 20:1 |
| HF/HC vol. ratio | 4:1 |
| Prefractionator (310): | |
| Pressure, psig. | 115 |
| Top Temperature, °F. | 125 |
| Bottom Temperature, °F. | 150 |
| HF Stripper (320): | |
| Pressure, psig. | 185 |
| Top Temperature, °F. | 150 |
| Bottom Temperature, °F. | 170 |
| Isostripper (330): | |
| Pressure, psig. | 230 |
| Top Temperature, °F. | 207 |
| Bottom Temperature, °F. | 416 |
| Vapor-Liquid Separator (340): | |
| Pressure, psig. | 35 |
| Temperature, °F. | 75 |
| Accumulator (350): | |
| Pressure, psig. | 75 |
| Temperature, °F. | 100 |
| Depropanizer (360): | |
| Pressure, psig. | 235 |
| Top Temperature, °F. | 120 |
| Bottom Temperature, °F. | 195 |
| Separator (370): | |
| Pressure, psig. | 230 Depends on |
| Temperature, °F. | 100 Operation |

Figure 4:
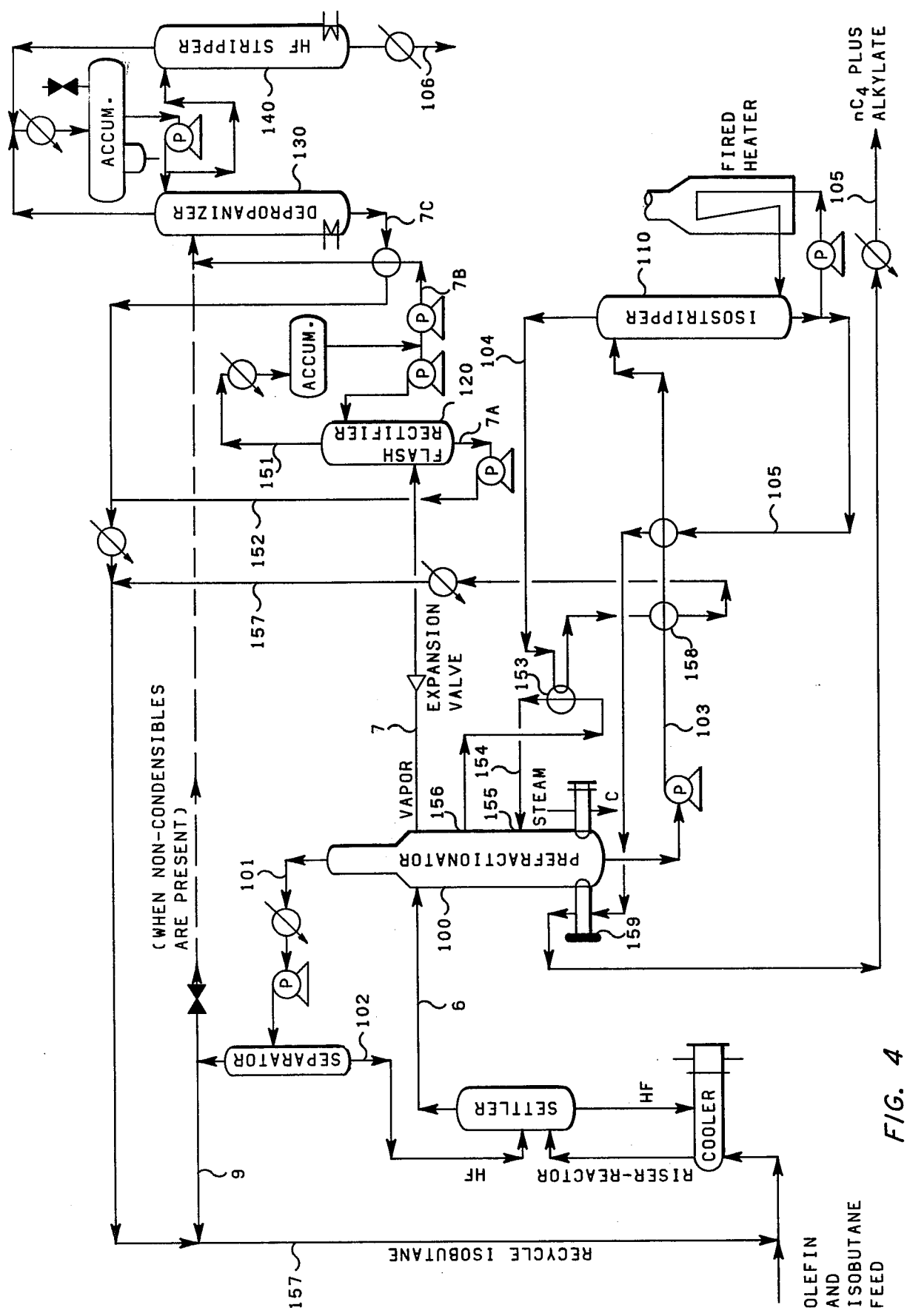
FIG. 4 discloses an alkylation system wherein a side stream is taken from the prefractionator and fed to a propane concentration zone which is a flashing zone. The overhead vapor from the flashing zone is then fed to the depropanizer. Overhead vapor from the isostripper, as well as bottoms from the isostripper, are used to reboil the prefractionator.

The embodiment shown in FIG. 4 discloses removing a vapor side cut 7 from the prefractionator 100 and is charged to "flash rectifier tower" 120. Most of the overhead vapor 151 is, after condensing, returned as reflux for tower 120 to concentrate the propane in the overhead yield 7b. A bottoms liquid 7a (from the reflux) is recycled as isobutane via 152. (Only that amount of propane charged in the feed and produced in the alkylation has to be removed via 7b to the depropanizer-HF stripper, ultimately out at 106.) This "flash tower" 120 operation produces an extremely (relatively) rich propane stream of relatively small amount to be charged to the depropanizer 130 via 7b. Bottoms 7c, which indirectly heats depropanizer feed 7b, is recycled (rich in isobutane) to alkylation. Unit 140 is the standard HF stripper to yield substantially HF-free propane at 106. The small concentrated propane feed stream allows for use of reduced pressure and utility, e.g., to reboil the depropanizer and the use of a smaller depropanizer unit altogether. The result is a lowering of energy requirements for the system.

The high pressure isostripper 110 produces high temperature isobutane vapor 104 used to reboil, at a lower side draw 153, the prefractionator 100. The vaporized prefractionator stream 154 is returned to the prefractionator at a point 155 below that of the take-off locus 156. The overhead vapor 104 is also used to preheat the isostripper feed 103 at 158 before being recycled to alkylation via 157.

Additional reboil of prefractionator 100 is effected with isostripper bottoms yield 105 and 159 after the bottoms pheheats feed 103 to the isostripper 110.

The hydrocarbon phase from the HF alkylation settler is passed via 6 to low pressure prefractionator 100. The HF-rich overhead 101 is passed after condensing and pumping to liquid-liquid separation. HF 102 is returned to the HF phase in the alkylation settler. The hydrocarbon liquid is added via 9 to recycled isobutane in 157. Bottoms 103 from prefractionator 100 is substantially HF-free and can be charged without corrosion problems to isostripper 110, operated at high pressure and high temperature. This allows yielding high temperature isobutane-rich vapor 104 which can heat the low pressure prefractionator 100 at 153, and high temperature liquid 105 to reboil this prefractionator at 159.

When noncondensibles are present in stream 9, at least a portion of stream 9 is charged to the depropanizer 130, as shown as unnumbered dashed line.

A calculated example of the embodiment shown in FIG. 4 is as follows:

| Component Stream | CALCULATED RUN barrels/day | | | | | |
|---|---|---|---|---|---|---|
| | HF | $C_3$ | $C_4$ | $nC_4$ | $iC_5$ plus | Total |
| (6) | 730 | 1,562 | 106,568 | 4,335 | 11,518 | 124,713 |
| (7) | 5 | 1,002 | 30,579 | 959 | 208 | 32,753 |
| (7a) | 0 | 447 | 28,766 | 949 | 208 | 30,370 |
| (7b) | 5 | 555 | 1,813 | 10 | 0 | 2,383 |
| (7c) | 0 | 203 | 1,808 | 10 | 0 | 2,021 |
| (9) | 122 | 521 | 13,114 | 390 | 25 | 14,172 |
| (101) | 725 | 522 | 13,114 | 390 | 25 | 14,776 |
| (102) | 603 | — | — | — | — | 603 |
| (103) | — | 38 | 62,875 | 2,986 | 11,285 | 77,184 |
| (104) | — | 38 | 62,849 | 2,468 | 1,174 | 66,529 |
| (105) | — | — | 26 | 518 | 10,111 | 10,655 |
| (106) | — | 352 | 5 | — | — | 357 |

| OPERATING CONDITIONS | |
|---|---|
| HF Alkylation: | |
| Pressure, psig. | 150 |
| Temperature, °F. | 90 |
| IC$_4$/Olefin mol ratio | 20.1 |
| HF/Total HC, vol. ratio | 4:1 |
| Prefractionator (100): | |
| Pressure, psig. | 115 |
| Top Temperature, °F. | 120 |
| Side Draw Temperature, °F. | 141 |
| Bottom Temperature, °F. | 150 |
| Propane Flash Tower (120): | |
| Pressure, psig. | 112 |
| Top Temperature, °F. | 119 |
| Bottom Temperature, °F. | 132 |
| Isostripper (110): | |
| Pressure, psig. | 230 |
| Top Temperature, °F. | 207 |
| Bottom Temperature, °F. | 416 |
| Depropanizer (130): | |
| Pressure, psig. | 245 |

| -continued | |
|---|---|
| OPERATING CONDITIONS | |
| Top Temperature, °F. | 119 |
| Bottom Temperature, °F. | 190 |
| HF Stripper (140): | |
| Pressure, psig. | 285 |
| Top Temperature, °F. | 132 |
| Bottom Temperature, °F. | 139 |

Reasonable variations and modifications can be made, or followed, in view of the foregoing disclosure, without departing from the spirit or scope thereof.

I claim:

1. An alkylation process which comprises:
   contacting an olefin and isoparaffin in the presence of an HF acid-alkylation catalyst under alkylation conditions to form an alkylation effluent comprising alkylate, isoparaffin, and acid catalyst,
   separating said effluent into an acid catalyst phase and hydrocarbon phase,
   passing said hydrocarbon phase to a fractionator wherein said hydrocarbon phase is separated into at least two fractions with a first fraction being a substantially HF free fraction which is passed to a propane concentration zone to thereby increase the concentration of propane in the feed stream to be sent to a depropanizer and a second fraction being an acid-catalyst rich overhead fraction,
   feeding the propane-rich fraction obtained from said propane concentration zone to a depropanizer from which purified propane is recovered,
   feeding a bottom fraction from said propane concentration zone to an isostripper thereby yielding an overhead vapor stream and a bottoms stream,
   passing in indirect heat exchange relationship at least one of said overhead vapor stream or said bottoms stream from the isostripper with at least one of said feed stream to said isostripper or as a heat source to said fractionation zone, thereby conserving energy by maximizing the use of available heat energy.

2. An alkylation process in accordance with claim 1 wherein said substantially HF free fraction passed to the propane concentration zone is a bottoms fraction taken from the fractionator.

3. A process in accordance with claim 2 wherein
   said isoparaffin is isobutane,
   said fractionator is a low pressure fractionator operated at a pressure not greater than 115 psig, and
   said isostripper is a high pressure isostripper.

4. A process in accordance with claim 2 wherein
   said overhead vapor stream from the isostripper is passed in indirect heat exchange relationship with the fractionator in order to reboil said fractionator zone and
   the bottoms stream of the isostripper is passed in indirect heat exchange relationship with the feed stream to the isostripper thereby preheating said feed stream.

5. A process in accordance with claim 2 wherein said propane concentration zone is a fractionation column.

6. A process in accordance with claim 5 wherein a sidestream is removed from said column and recycled to said contacting,
   the overhead vapor stream from the isostripper is passed in indirect heat exchange relationship with the propane concentration zone and in indirect heat exchange relationship with the fractionator in order to supply heat for the reboiling of said zone and said fractionator, and the bottoms from the isostripper is passed in indirect heat exchange relationship with the feed to the isostripper.

7. A process in accordance with claim 2 wherein said propane concentration zone is a flashing zone.

8. A process in accordance with claim 7 wherein the overhead from the propane concentration zone is passed to a second flashing zone and the overhead from said second flashing zone is then passed to the depropanizer, the overhead vapor from the isostripper is passed in indirect heat exchange relationship with the fractionator, in order to reboil said fractionator, in indirect heat exchange relationship with said catalyst-free bottoms recovered from the fractionator and in indirect heat exchange relationship with said feed to the isostripper in order to preheat said feed stream, and the isostripper bottoms is passed in indirect heat exchange relationship with the feed stream to the isostripper.

9. A process in accordance with claim 7 wherein said flashing zone is the acid catalyst cooling zone to thereby cool the catalyst by flashing, overhead vapor from said flashing is passed to the depropanizer, the overhead vapor from the isostripper is passed in indirect heat exchange relationship with the fractionator, in order to reboil said fractionator, and in indirect heat exchange relationship with the feed stream to the isostripper, isostripper bottoms is passed in indirect heat exchange relationship with the feed stream to the isostripper, and the fractionator bottoms is passed in indirect heat exchange with the feed stream to the fractionator and the feed stream to the isostripper.

10. An alkylation process which comprises:

contacting an olefin and isoparaffin in the presence of an HF acid alkylation catalyst under alkylation conditions to form an alkylation effluent comprising alkylate, isoparaffin, and acid catalyst, separating said effluent into an acid catalyst phase and hydrocarbon phase, passing said hydrocarbon phase to a fractionator wherein said hydrocarbon phase is separated into at least two fractions with a first fraction being a substantially HF free fraction with said substantially HF free fraction being a side fraction which is passed to a propane concentration zone which is a flashing zone to thereby increase the concentration of propane in the feed stream to be sent to a depropanizer and a second fraction being an acid-catalyst rich overhead fraction, recovering an overhead and bottoms fraction from the flashing zone, passing the overhead fraction, which is propane-rich, from the flashing zone to a depropanizer whereas the bottoms fraction from the flashing zone is recycled to alkylation, feeding the bottoms fraction to the fractionator to an isostripper thereby yielding an overhead vapor stream and a bottoms stream, and passing in indirect heat exchange relationship at least one of said overhead vapor stream or said bottoms stream from the isostripper with at least one of said feed stream to said isostripper or as a heat source to said fractionation zone, thereby conserving energy by maximizing the use of available heat energy.

11. A process in accordance with claim 10 wherein the overhead vapor from the isostripper and the bottoms from the isostripper are passed in indirect heat exchange relationship with the fractionator to reboil said zone and in indirect heat exchange relationship with the feed stream to the isostripper to preheat said stream.

12. A process in accordance with claim 9 wherein the acid-catalyst rich overhead froction taken form the fractionator is separated into its hydrocarbon and acid catalyst phases with the acid phase being recycled to said separating wherein alkylation effluent is separated into an acid catalyst phase and hydrocarbon phase and the hydrocarbon phase is passed to the propane concentration zone.

* * * * *